United States Patent
Rooney (12)

(10) Patent No.: US 6,353,138 B1
(45) Date of Patent: Mar. 5, 2002

(54) PROCESS FOR PURIFYING AQUEOUS TERTIARY AMINE AND ALKANOLAMINE SOLUTIONS

(76) Inventor: Peter C. Rooney, 62 S. Callalily Ct., Lake Jackson, TX (US) 77566

( * ) Notice: Subject to any disclaimer, the term of this patent is extended or adjusted under 35 U.S.C. 154(b) by 0 days.

(21) Appl. No.: 09/551,459

(22) Filed: Apr. 18, 2000

Related U.S. Application Data

(60) Provisional application No. 60/134,903, filed on May 19, 1999.

(51) Int. Cl.[7] .............................................. C07C 209/84
(52) U.S. Cl. ...................................... 564/497; 564/499
(58) Field of Search ................................. 564/497, 499

(56) References Cited

U.S. PATENT DOCUMENTS 5,292,958 A * 3/1994 Claud et al. ................ 564/499
5,481,037 A * 1/1996 Fuchs et al. ................ 564/437

OTHER PUBLICATIONS

Rooney, et al., Effect of Heat Stable Salts on Corresivity of MDEA–Based Aldanolamine Plants Part III, The Proceedings of the 48th Annual Laurance Reid Gas Conditioning Conference, pp. 12–30, Mar. 1–4, 1998.

Rooney, et al., The Role of Oxygen in the Degradation of MEA, DGA, DEA and MDEA, The Proceedings of the 48th Annual Laurance Reid Gas Conditioning Conference, pp. 335–347, Mar. 1–4, 1998.

A. Chakma and A. Meisen, *The Canadian Journal of Chemical Engineering*, vol. 75, pp. 861–871, Oct. 1997.

O. F. Dawodu and A. Meisen, *The Canadian Journal of Chemical Engineering*, vol. 74, pp. 960–966, Dec., 1996.

M. L. Kennard and A. Meisen, *Journal of Chromatography*, vol. 267, pp. 373–380, 1983.

A. Chakma and A. Meisen, *Carbon*, vol. 27, No. 4, pp. 573–584, 1989.

\* cited by examiner

*Primary Examiner*—Johann Richter
*Assistant Examiner*—Brian J. Davis
(74) *Attorney, Agent, or Firm*—Garvey, Smith, Nehrbass & Doody, LLC

(57) ABSTRACT

A process for the removal of primary and secondary amine and alkanolamine impurities from aqueous tertiary amine and alkanolamine solutions without affecting the tertiary amine and/or alkanolamine by treating these solutions with a monoaldehyde or dialdehyde has been described.

11 Claims, No Drawings

PROCESS FOR PURIFYING AQUEOUS TERTIARY AMINE AND ALKANOLAMINE SOLUTIONS

CROSS REFERENCE STATEMENT

This application claims the benefit of U.S. Provisional Application No. 60/134,903, filed on May 19, 1999.

This invention relates to a process for removing primary and secondary amine and alkanolamine impurities from aqueous tertiary amine and alkanolamine solutions used for removal of acid gases from a fluid stream containing same.

BACKGROUND OF THE INVENTION

Purification of fluids involves removal of impurities from fluid steams. Various fluid purification methods are known and practiced. These fluid purification methods generally fall in one of the following categories: absorption into a liquid, adsorption on a solid, permeation through a membrane, chemical conversion to another compound, and condensation. The absorption purification method involves the transfer of a component of a fluid to a liquid absorbent in which said component is soluble. If desired, the liquid containing the transferred component is subsequently stripped to regenerate the liquid. See, for example, A. Kohl and R. Nielsen, Gas Purification, $5^{th}$ edition, Gulf Publishing, 1997; incorporated herein by reference.

Aqueous solutions of various primary, secondary and tertiary alkanolamines, such as, for example, monoethanolamine (MEA), diethanolamine (DEA), methyldiethanolamine (MDEA) and triethanolamine (TEA), have been widely used as absorbent liquids to remove acid gases such as carbon dioxide ($CO_2$), hydrogen sulfide ($H_2S$), carbonyl sulfide (COS) and carbon disulfide ($CS_2$) from liquid and gas streams. In a regeneration method, the aqueous alkanolamine solution containing acid gas is then subjected to heat to regenerate the aqueous alkanolamine solution.

Primary alkanolamines such as MEA or secondary alkanolamines such as DEA are known to be very reactive and thus generally suitable for highly exhaustive removal of $CO_2$, however they have disadvantage of requiring large expenditure of energy for regeneration.

Tertiary alkanolamines, especially MDEA and TEA, require less energy consumption for regeneration, and since they do not react directly with $CO_2$, they are often used for selective removal of $H_2S$ from a fluid stream containing both $H_2S$ and $CO_2$.

The chemistry of acid gas reactions with aqueous alkanolamine treating solutions is well known and is described in many publications such as, for example, the aforementioned publication and references cited therein.

It is known that oxygen can degrade MDEA to form DEA impurities [about 1600 parts per million (ppm) DEA]. See, Rooney at al, The Proceedings of the $48^{th}$ Annual Laurance Reid Gas Conditioning Conference, March 1–4, 1998, p. 335–347, incorporated herein by reference.

Thermal degradation of tertiary alkanolamines has also been reported to form primary and secondary amine and alkanolamine impurities such as N,N,N-tris(2-hydroxyethyl)ethylenediamine (THEED), DEA and methylaminoethanol (MAE). See, for example, A. Chakma and A. Meisen, The Canadian Journal of Chemical Engineering, vol. 75, pp 861–871; and O. F. Dawodu and A. Meisen, The Canadian Journal of Chemical Engineering, vol. 74, pp 960–966, both incorporated herein by reference. In addition, it has been reported that DEA formed a secondary amine impurity identified as 4-(2-hydroxyethyl)piperazine (HEP). See, M. L. Kennard and A. Meisen, Journal of Chromatography, vol. 267, pp 373–380.

For gas treating applications where tertiary alkanolamines such as MDEA and TEA are used to selectively remove $H_2S$ in the presence of $CO_2$, the presence of primary alkanolamines such as MEA, secondary alkanolamines such as MAE and DEA, or secondary amines such as HEP will cause the reaction of $CO_2$ to increase, resulting in reduced $H_2S$ removal. This increases costs by having to increase the amine circulation rate and/or having to lower the gas flow rate. For plants having an additional sulfur recovery unit, this increased $CO_2$ and decreased $H_2S$ reaction results in increased operational difficulties such as having to increase the oxygen content to the burner, corrosion concerns and other increased costs for the sulfur unit.

Up to now, the practice used in the industry for removing primary and secondary amine and alkanolamine impurities from solutions of MDEA and/or TEA is to use vacuum distillation. However, this process is expensive since the whole system volume of the plant must be vacuum distilled. In addition, it is extremely difficult to remove DEA from especially MDEA because the boiling point of each is somewhat similar. Also, having to remove small amounts of impurities by distillation often requires high losses of the desired tertiary alkanolamine.

A. Chakma and A. Meisen in Carbon, Volume 27, No. 4, p 573–584, (1984) have reported the use of activated carbon to remove degradation products of DEA and MDEA, however, it is shown that activated carbons has very low capacity and become saturated within short periods of time.

U.S. Pat. No. 5,292,958 (Blanc and Claud) discloses a process in which DEA impurities in TEA are removed using glyoxal. However, it is taught that greater than 1 equivalent of glyoxal is required, and when this is done that bicine is the reaction product. As has been disclosed in Rooney et. al in The Proceeding of the 1997 Laurance Reid Gas Conditioning Conference (p 12–30), bicine is a particularly corrosive agent in alkanolamine plants.

There is still a great need and interest for the removal of primary and secondary amine and alkanolamine impurities from aqueous tertiary amine and alkanolamine solutions used for removing acid gases from a fluid stream.

It has now been discovered that primary and secondary amine and alkanolamine impurities can be removed from aqueous tertiary amine and alkanolamine solutions without affecting the tertiary amine and/or alkanolamine by treating these solutions with a monoaldehyde or dialdehyde.

In the context of the present invention the term "fluid stream" encompasses both a gaseous stream and liquid stream.

SUMMARY OF THE INVENTION

In one embodiment the present invention is a process for removing primary and secondary amine and alkanolamine impurities from an aqueous tertiary amine or alkanolamine solution used for removal of acid gases from a fluid stream which process comprises treating the aqueous amine or alkanolamine solution with a monoaldehyde.

In another embodiment the present invention is a process for removing primary and secondary amine and alkanolamine impurities from an aqueous tertiary amine or alkanolamine solution used for removal of acid gases from a fluid stream which process comprises treating the aqueous amine or alkanolamine solution with less than one equivalent of a dialdehyde per equivalent of the amine or alkanolamine in the solution treated.

DETAILED DESCRIPTION OF THE INVENTION

Without being bound by theory, it is believed that the aldehyde reacts with the primary and secondary alkanolamine to form a tertiary oxazolidine. This tertiary oxazolidine (a tertiary amine) would be expected to have much lower reactivity with $CO_2$ than the parent primary or secondary amine or alkanolamine. This tertiary oxazolidine may stay in the solution as a stable tertiary amine, part may revert back to the parent amine or alkanolamine, or, under reducing conditions in which the gas stream contains hydrogen, or optionally, if hydrogen is added to the gas stream, the oxazolidine may further react to form a stable tertiary amine or alkanolamine (see, for example, Eq. 1 showing the reaction of DEA and formaldehyde forming oxazolidine-3-ethanol, which then can react with hydrogen to form a tertiary alkanolamine, MDEA). Surprisingly, When less than 1 equivalent of a dialdehyde is used, the amount of bicine formed is kept very low while also forming a high conversion of the DEA.

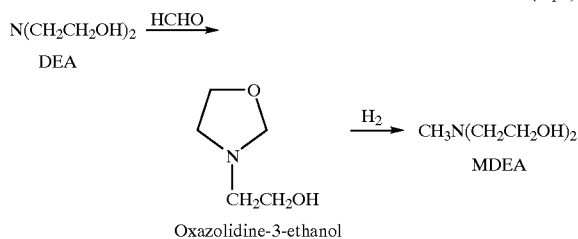

Any known monoaldehyde can be used in the process of the present invention. Non-limiting examples of suitable monoaldehydes include formaldehyde, acetaldehyde, propionaldehyde and the like. Formaldehyde is the preferred monoaldehyde. The amount of monoaldehyde used is not critical but it is preferred to use from about 0.01 to about 1.5 equivalents of the monoaldehyde per one equivalent of the primary and secondary amine or alkanolamine in the solution treated. More than 1.5 equivalents of aldehyde may be used, but care must be taken that excess aldehyde can react with $H_2S$ to form solid trithianes which may precipitate in the solution to be treated. The exact amount of monoaldehyde required can be easily determined by experimentation. When adding the monoaldehyde to a circulating plant solution treating acid gas, enough monoaldehyde should be added to increase the $CO_2$ slip to a desired level. Especially when monoaldehyde is added to a circulating plant solution, losses of the monoaldehyde out the absorber or stripper, or by reaction with $H_2S$ may require additional monoaldehyde to be added that is calculated based upon primary and secondary amine or alkanolamine in the solution. When adding the monoaldehyde to a storage vessel of amine or alkanolamine solution, enough monoaldehyde should be added to decrease the concentration of primary and secondary amine or alkanolamine to a desired level.

Any known dialdehyde can be used in the process of the present invention. Non-limiting examples of suitable dialdehydes include glyoxal, methylglyoxal, dimethyl-glyoxal and the like. Glyoxal is the preferred dialdehyde. It is important to use the dialdehyde in an amount such that less than one, preferably from about 0.01 to about 0.99, more preferably from about 0.5 to about 0.99,equivalent of the dialdehyde is used per one equivalent of the amine or alkanolamine in the solution treated to reduce or eliminate formation of bicine which is particularly corrosive agent in the alkanolamine plants.

The monoaldehyde or dialdehyde can be added to a circulating plant solution over a period of time, preferably over a period of about 1–22, more preferably over a period of about 1–12 hours. The exact time of addition is relatively unimportant, but too fast an addition may result in unreacted aldehyde being lost with the incoming gas going to the top of the absorber. The preferred addition point is in the lean amine coming from the plant cross exchanger to the absorber. Additions of monoaldehyde or dialdehyde could be made in the lean amine line coming from the bottom of the stripper going to the cross exchanger. Alternatively, additions could be made to the rich amine at the bottom of the absorber; however, any $H_2S$ present may consume some of the aldehyde to form undesirable solids. The amount of aldehyde should at least be a minimum amount such that an improvement in $CO_2$ slip, and/or $H_2S$ removal results. Excess aldehyde may be carried out with the absorber or stripper, or may react with $H_2S$ to form insoluble trithianes. Additional aldehyde may then be added so that the desired $CO_2$ slip and/or $H_2S$ removal is achieved.

If desired, hydrogen can be added to the circulating amine or alkanolamine solution that has been treated with aldehyde or dialdehyde. In this embodiment of the present invention, any oxazolidines that are formed are at least partially converted to very stable tertiary amines or alkanolamine. Optionally, a hydrogenation bed consisting of, for example, Raney Ni may be used to pass the aldehyde-treated circulating solution through to further improve the efficiency of oxazolidine conversion to tertiary amine and/or alkanolamine.

Also, in the process of the present invention a solution of tertiary amine and/or alkanolamine can be reacted with aldehyde in a vessel and then reclaimed by distillation or vacuum distillation to remove the oxazolidine and/or other impurities. In this embodiment of the present invention, for example, DEA may be converted to a lower boiling oxazolidine-3-ethanol that is much more easily separated from MDEA and/or TEA than could be performed without the addition of aldehyde. Optionally, hydrogenation of this aldehyde-treated solution may be performed to further reduce the primary and/or secondary amine and/or alkanolamine amount that is in the distilled product. Also, a hydrogenation bed consisting of, for example, Raney Ni may be used to pass the aldehyde-treated solution through to further improve the efficiency of oxazolidine conversion to tertiary amine and/or alkanolamine.

The following examples are offered to illustrate but not limit the invention. Percentages, ratios and parts are by weight unless stated otherwise.

EXAMPLE 1—Reaction of a Mixture of MDEA, MMEA and DEA with Formaldehyde

A synthetic mixture (500 g) containing 1.01 weight percent MAE, 1.01 weight percent DEA, 50.31 weight percent MDEA, 46.44 weight percent water and 1.24 weight percent $CO_2$ was prepared. This solution (75 g.) was reacted with formaldehyde (1 equivalent of formaldehyde per equivalent of DEA and MMEA combined and also 2 equivalents of formaldehyde per equivalent of DEA and MMEA combined) and then the two reaction solutions were heated at 123° F. for 5 days. The formaldehyde solution used in these experiments was 37 weight percent formaldehyde containing 10 weight percent methanol (balance water). The reaction of 1 equivalent of formaldehyde results in an immediate decrease at 15 minutes reaction time of 0.99 weight percent MAE and DEA to about 0.1 weight percent MAE and 0.18 weight percent DEA. A new peak, identified as oxazolidine-3-ethanol, appears as 0.78 area percent by gas chromatography (GC). The reaction with 2 equivalents of formaldehyde, no MAE or DEA is detected by GC, and the peak identified as oxazolidine-3-ethanol appears as 1.0 area percent by GC. After heating for 5 days at 123° F., there is very little change in concentration of each of MAE, DEA or oxazolidine-3-ethanol.

EXAMPLES 2—Reaction of a Mixture of MDEA, MMEA and DEA with Glyoxal at 123° F. for 5 days The procedure of Example 1 was repeated except that glyoxal (1 equivalent and 2 equivalents per equivalent of DEA and MAE combined) was used instead of formaldehyde. The glyoxal solution used in these experiments was 40 weight percent glyoxal in water. The reaction of glyoxal results in an immediate decrease at 15 minutes reaction time of 0.99 weight percent MAE and DEA to less than 0.03 weight percent MAE or DEA. Three unidentified new peaks at retention time 4.1, 8.98 and 11.18 minutes appear. After heating the reaction solution for 5 days at 123° F., the MAE, DEA and the 11.18 minute retention time peaks increase slowly, and the unknown peaks at 4.1 and 8.98 minutes increase. No attempt was made to identify any of the new peaks by gas spectroscopy/mass spectroscopy (GC/MS).

EXAMPLES 3—Reaction of a Mixture of MDEA, MAE, DEA and Piperazine with Formaldehyde at 214° F. for 5 days A synthetic mixture (500g) containing 1.12 weight percent MAE, 1.55 weight percent DEA, 1.32 weight percent piperazine, 51.64 weight percent MDEA, 42.90 weight percent water and 1.47 weight percent $CO_2$ was prepared. This solution (75 g.) was reacted with formaldehyde (1 equivalent of formaldehyde per equivalent of DEA and MAE combined and also 2 equivalents of formaldehyde per equivalent of DEA and MAE combined) and each of the reaction solutions was then heated at 214° F. for 5 days. The formaldehyde solution used in these experiments was 37 weight percent formaldehyde containing 10 weight percent methanol (balance water). The reaction of 1 equivalent of formaldehyde results in an immediate decrease at 15 minutes reaction time of piperazine to about 0.2 weight percent. No MAE or DEA was detected by GC. Two new peaks, identified by GC/MS as dimethylethanolamine (DMEA) and oxazolidine-3-ethanol, appear as 0.1 area percent and 1.5 area percent respectively, by GC. The concentrations of MAE, DEA and DMEA all increase to about 0.6 weight percent, 1.1 weight percent and 0.7 weight percent, respectively over a 60 hour time period, while the concentration of oxazolidine 3-ethanol decreases over time. Piperazine remains constant at 0.2 weight percent.

The reaction of 2 equivalents of formaldehyde resulted in no MAE or DEA detection by GC, and piperazine is detected at 0.06 weight percent after 15 minutes reaction time. The concentration of oxazolidine-3-ethanol is 1.34 area percent. The concentrations of piperazine and MAE remain less than 0.1 weight percent after heating for 5 days at 214° F. The concentration of DEA rises slowly to 0.2 weight percent after 5 days. The concentration of DMEA increases to 1.4 area percent while the concentration of oxazolidine-3-ethanol decreases to about 0.1area percent after 5 days. Dimethylpiperazine was also detected by GC/MS, but could not be quantitated by GC since it co-elutes with water.

EXAMPLE 4—Reaction of a Mixture of MDEA, MAE, DEA and Piperazine with Glyoxal at 214° F for 5 days The procedure of Example 3 was repeated except that glyoxal (1 equivalent and 2 equivalents per equivalent of DEA and MAE combined) was used instead of formaldehyde. The glyoxal solution used in these experiments was 40 weight percent glyoxal in water. The reaction of glyoxal results in an immediate decrease at 15 minutes reaction time of MAE and DEA to less than 0.05 weight percent MMEA or DEA. Piperazine concentration was reduced from 1.26 weight percent to 0.95 and 0.21 weight percent using 1 and 2 equivalents, respectively of glyoxal. Five unidentified new peaks at retention time 3.9, 4.1, 8.9, 10.2 and 11.18 minutes appear. After heating for 5 days at 214° F., the MAE and DEA concentration increases slowly to about 0.25 weight percent, while the concentration of the 5 unidentified peaks remains constant at about 0.7 area percent for the 3.9 and 4.1 retention time peaks and 1.1 area percent for the 8.9, 10.2 and 11.18 retention time peaks. Piperazine increased steadily over time to 1.2 weight percent and 0.9 weight percent using 1 and 2 equivalents, respectively of glyoxal. No attempt was made to identify any of the new peaks by GC/MS.

EXAMPLE 5—Reaction of Refinery Plant Solution with Formaldehyde

A refinery plant solution containing 49 percent methyldiethanolamine (MDEA) was used in this Example. A solvent analysis of the solution showed that the solution contained 0.0002 M/M $CO_2$, 0.0005 M/M $H_2S$, 0.74 weight percent diethanolamine (DEA) and 0.52 weight percent methylmonoethanolamine (MMEA). When 10 g. of this plant solution, containing 0.00142 moles of MMEA and DEA, was reacted with 0.00142 moles of formaldehyde (37 weight percent in water containing 10 percent methanol, balance water) at room temperature in a flask, gas chromatography (GC) analysis showed that only 0.20 weight percent DEA and 0.089 weight percent of MAE remained. One new peak at 5.3 minutes appeared (0.44 area percent) that was identified by GC/MS as the tertiary amine oxazolidine-3-ethanol. When 10 g. of this plant solution, containing 0.00142 moles of MMEA and DEA, was reacted with 0.00284 moles of formaldehyde (37 weight percent in water containing 10 percent methanol, balance water) at room temperature in a flask, GC analysis showed that only 0.03 weight percent DEA remained. MAE was not detected by GC. One new peak at 5.3 minutes appeared (0.60 area percent) that was identified by GC/MS as the tertiary amine oxazolidine-3-ethanol.

EXAMPLE 6—Reaction of Refinery Plant Solution with Glyoxal

The refinery plant solution (5 g.) described in Example 5, containing 0.00071 moles of MMEA and DEA, was reacted with 0.00284 moles of glyoxal (40 weight percent in water) at room temperature in a flask. The GC analysis showed that only 0.07 weight percent DEA and 0.15 weight percent MAE remained after the reaction. One new peak at 11.2 minutes appeared (0.42 area percent) that was not analyzed by GC/MS.

EXAMPLE 7—Reaction of a Natural Gas Plant Operating Solution with Formaldehyde A natural gas plant having a 11,600 gallon circulating solution of about 35 weight percent MDEA, 0.41 weight percent DEA and 0.37 weight percent MAE was used for this Example. $CO_2$ slip with a fresh solution of MDEA had been excellent (>90 percent slip), however, as the MAE and DEA concentration increased, $CO_2$ slip deteriorated to about 70 percent. One 55 gallon drum of 37 weight percent formaldehyde (roughly 1 equivalent of formaldehyde per equivalent of MAE and DEA combined) was added to the plant circulating solution between the lean amine exchanger and the absorber over a period of 5 days. It had been proposed to add the 55 gallons of formaldehyde solution over a 6–10 hour period, which would have resulted in about 6–10 system volumes to circulate past the injection point, but pump problems resulted in the addition taking much longer. After the addition was complete, the plant $CO_2$ analyzer showed that the $CO_2$ slip had increased to greater than 90 percent. Analysis of the solution showed that the DEA and MAE had decreased to 0.34 and 0.31 weight percent, respectively. This corresponds to about a 17 weight percent drop in DEA and MAE combined.

EXAMPLE 8—Reaction of a Solution of MDEA and DEA with Glyoxal or Formaldehyde A stock solution was made that contained 45 weight percent MDEA, 5.2 weight percent DEA and the balance water. To 100 g portions of the stock solution were added either 0.25, 0.5, 1 or 2 equivalents of glyoxal or 2 mole equivalents of formaldehyde. The solutions were stirred for 1 hour and then analyzed by GC and GC/MS. The results in Table 1 below show that a significant amount of bicine is formed when 1 equivalent of glyoxal or greater is used. For comparison, when 2 equivalents of formaldehyde (8.02 g. of 37 weight percent in water) was reacted with 100 g of the stock solution no bicine was formed.

This data shows that by using more than 1 equivalent of glyoxal that high conversions of DEA can be done without forming large amounts of the known corrosive agent bicine.

TABLE 1

Reaction of 100 g. of amine solution containing 5.2 g (49.5 mmoles) DEA after 1 hour.

| Exp. No. | grams DEA remaining in solution | grams of 40 wt. % glyoxal | equivalents glyoxal | mmoles DEA reacted (% DEA reacted) | Bicine wt. % (mmoles) |
|---|---|---|---|---|---|
| 0 | 5.2 | 0 | 0 | 0 | 0 |
| 1 | 3.3 | 1.81 | 0.25 | 17.2 (35%) | 0.03 (0.45) |
| 2 | 1.7 | 3.63 | 0.50 | 33.3 (67%) | 0.15 (2.3) |
| 3* | N.D.** | 7.25 | 1.0 | 49.5 (100%) | 1.1 (16.9) |
| 4* | N.D.** | 14.5 | 2.0 | 49.5 (100%) | 2.5 (38.3) |

*:Not an Example of the present invention
**:N.D. means not detected

EXAMPLE 9—Reaction of a Solution of MDEA and DEA with Glyoxal or Formaldehyde The procedure of Example 8 was repeated except that the reaction was allowed to proceed for 22 hours. The results in Table 2 below show about 90 percent conversion of DEA with very small amounts of bicine formed when DEA is reacted with less than 1 equivalent of glyoxal. For comparison, when 2 equivalents of formaldehyde (8.02 g. of 37 weight percent in water) was reacted with 100 g. of the stock solution for 22 hours no bicine was formed and the solution remained clear of color.

TALBE 2

Reaction of 100 g. of amine solution containing 5.2 g. (49.5 mmoles) DEA after 22 hours.

| No | Color | g. DEA remaining in solution | g of 40 wt. % glyoxal | equivalents glyoxal | mmoles DEA reacted (% DEA reacted) | Bicine wt. % (mmoles) |
|---|---|---|---|---|---|---|
| 0 | clear | 5.2 | 0 | 0 | 0 | 0 |
| 1 | clear | 3.3 | 1.81 | 0.25 | 22.5 (45%) | 0 |
| 2 | clear | 1.7 | 3.63 | 0.50 | 4.8 (90%) | 0.09 (0.58) |
| 3* | yellow/orange | N.D.** | 7.25 | 1.0 | 49.5 (100%) | 4.5 (27.5) |
| 4* | dark orange | N.D.** | 14.5 | 2.0 | 49.5 (100%) | 11.3 (69.2) |

*:Not an Example of the present invention
**:N.D. means not detected

What is claimed is:

1. A process for removing primary and secondary amine and alkanolamine impurities from an aqueous tertiary amine or alkanolamine solution used for removal of acid gases from a fluid stream which process comprises treating the aqueous amine or alkanolamine solution with a monoaldehyde in an amount of from about 0.01 to about 1.0 equivalent of the monoaldehyde per one equivalent of the amine or alkanolamine.

2. The process according to claim 1 wherein the monoaldehyde is formaldehyde.

3. The process according to any one of claims 1 to 2 wherein the monoaldehyde is added to a circulating amine or alkanolamine plant solution over a period of about 1 to 22 hours.

4. The process according to any one of claims 1 to 2 wherein the amine or alkanolamine solution is treated with the monoaldehyde in a vessel and then reclaimed by distillation or vacuum distillation.

5. The process according to claim 1 or claim 2 wherein the monoaldehyde and hydrogen are added to the circulating amine or alkanolamine plant solution.

6. A process for removing primary and secondary amine and alkanolamine impurities from an aqueous tertiary amine or alkanolamine solution used for removal of acid gases from a fluid stream which process comprises treating the aqueous amine or alkanolamine solution with less than one equivalent of a dialdehyde per equivalent of the amine or alkanolamine.

7. The process according to claim 6 wherein the dialdehyde is used in an amount of about 0.01 to about 0.99 equivalent of a dialdehyde per equivalent of the amine or alkanolamine in the solution treated.

8. The process according to claim 6 wherein the dialdehyde is glyoxal.

9. The process according to any one of claims 6 to 8 wherein the dialdehyde is added to a circulating amine or alkanolamine plant solution over a period of about 1 to 22 hours.

10. The process according to any one of claims 6 to 8 wherein the amine or alkanolamine solution is treated with the dialdehyde in a vessel and then reclaimed by distillation or vacuum distillation.

11. The process according to any one of claims 6 to 8 wherein the dialdehyde and hydrogen are added to the circulating amine or alkanolamine plant solution.

* * * * *